United States Patent [19]
Yoon

[11] Patent Number: 5,797,888
[45] Date of Patent: Aug. 25, 1998

[54] CANNULA WITH UNIVERSAL SEAL AND METHOD OF INTRODUCING INSTRUMENTS THERETHROUGH

[76] Inventor: InBae Yoon, 2101 Highland Ridge Dr., Phoenix, Md. 21131

[21] Appl. No.: 672,843

[22] Filed: Jul. 25, 1996

Related U.S. Application Data

[63] Continuation-in-part of Ser. No. 618,328, Mar. 19, 1996.

[51] Int. Cl.$^6$ ..................................................... A61M 25/00
[52] U.S. Cl. ........................... 604/280; 604/256; 604/249
[58] Field of Search ................................... 604/167, 256, 604/249, 264, 280

[56] References Cited

U.S. PATENT DOCUMENTS

| | | | |
|---|---|---|---|
| 1,986,484 | 11/1935 | Schlueter . | |
| 3,565,078 | 2/1971 | Vailliancourt . | |
| 3,585,996 | 6/1971 | Reynolds | 604/158 |
| 3,620,500 | 11/1971 | Santomieri . | |
| 3,721,229 | 3/1973 | Panzer | 604/278 |
| 3,994,287 | 11/1976 | Turp et al. . | |
| 4,023,559 | 5/1977 | Gaskell | 604/280 |
| 4,177,814 | 12/1979 | Knepshield et al. . | |
| 4,180,068 | 12/1979 | Jacobsen et al. . | |
| 4,240,411 | 12/1980 | Hosono . | |
| 4,243,034 | 1/1981 | Brandt . | |
| 4,475,548 | 10/1984 | Muto . | |
| 4,535,773 | 8/1985 | Yoon . | |
| 4,650,459 | 3/1987 | Sheldon . | |
| 4,654,030 | 3/1987 | Moll et al. . | |
| 4,681,110 | 7/1987 | Wiktor | 604/194 |
| 4,842,591 | 6/1989 | Luther . | |
| 4,850,969 | 7/1989 | Jackson . | |
| 4,874,378 | 10/1989 | Hillstead . | |
| 4,899,729 | 2/1990 | Gill et al. . | |
| 4,917,668 | 4/1990 | Haindl | 604/167 |
| 4,929,235 | 5/1990 | Merry et al. . | |
| 4,978,341 | 12/1990 | Neiderhauser | 604/167 |
| 4,994,027 | 2/1991 | Farrell . | |
| 5,073,168 | 12/1991 | Danforth | 604/167 |
| 5,085,636 | 2/1992 | Burns | 604/167 |
| 5,104,389 | 4/1992 | Deem et al. . | |
| 5,108,380 | 4/1992 | Herlitze et al. . | |
| 5,114,407 | 5/1992 | Burbank . | |
| 5,122,122 | 6/1992 | Allgoood | 604/167 |
| 5,127,626 | 7/1992 | Hilal et al. . | |
| 5,141,498 | 8/1992 | Christian | 604/167 |
| 5,156,596 | 10/1992 | Balbierz et al. | 604/264 |
| 5,158,553 | 10/1992 | Berry et al. . | |
| 5,161,773 | 11/1992 | Tower | 604/167 |
| 5,167,636 | 12/1992 | Clement . | |
| 5,176,659 | 1/1993 | Mancini . | |
| 5,180,373 | 1/1993 | Green et al. . | |
| 5,188,607 | 2/1993 | Wu | 604/167 |
| 5,195,980 | 3/1993 | Catlin | 604/167 |
| 5,197,955 | 3/1993 | Stephens et al. . | |
| 5,201,714 | 4/1993 | Gentelia et al. . | |
| 5,207,656 | 5/1993 | Kranys . | |
| 5,242,412 | 9/1993 | Blake, III | 604/167 |
| 5,269,763 | 12/1993 | Boehmer et al. | 604/167 |
| 5,282,790 | 2/1994 | Clement . | |
| 5,300,035 | 4/1994 | Clement . | |
| 5,300,047 | 4/1994 | Beurrier . | |
| 5,308,336 | 5/1994 | Hart et al. . | |

(List continued on next page.)

FOREIGN PATENT DOCUMENTS

| | | |
|---|---|---|
| 6465451 | 3/1989 | Japan . |
| 540629 | 12/1976 | U.S.S.R. . |

*Primary Examiner*—Corrine M. McDermott

[57] ABSTRACT

A cannula for insertion through an anatomical cavity wall to establish communication with the anatomical cavity includes an elongate tubular body having a distal end adapted to be disposed within the anatomical cavity and a proximal end adapted to be disposed externally of the anatomical cavity, a seal including a seal member disposed along the tubular body of the cannula, and a tubular pusher disposed in the tubular body and insertable through the seal to move the seal member from a normally closed position preventing fluid flow through the cannula to an open position allowing instruments of various sizes to be introduced through the tubular body via the tubular pusher without contacting the seal.

19 Claims, 2 Drawing Sheets

U.S. PATENT DOCUMENTS

| | | |
|---|---|---|
| 5,318,532 | 6/1994 | Frassica . |
| 5,320,611 | 6/1994 | Bonutti et al. ............................ 604/264 |
| 5,324,270 | 6/1994 | Kayan et al. . |
| 5,334,164 | 8/1994 | Guy et al. . |
| 5,336,203 | 8/1994 | Goldhardt et al. . |
| 5,350,362 | 9/1994 | Stouder, Jr. . |
| 5,350,364 | 9/1994 | Stephens et al. . |
| 5,350,393 | 9/1994 | Yoon . |
| 5,354,280 | 10/1994 | Haber et al. . |
| 5,360,403 | 11/1994 | Mische . |
| 5,360,417 | 11/1994 | Gravener et al. . |
| 5,366,478 | 11/1994 | Brinkerhoff et al. . |
| 5,385,553 | 1/1995 | Hart et al. . |
| 5,389,080 | 2/1995 | Yoon ......................................... 604/167 |
| 5,391,153 | 2/1995 | Haber et al. . |
| 5,429,609 | 7/1995 | Yoon . |
| 5,437,626 | 8/1995 | Cohen et al. ............................ 604/167 |
| 5,441,486 | 8/1995 | Yoon . |
| 5,460,616 | 10/1995 | Weinstein . |
| 5,476,475 | 12/1995 | Gadberry . |
| 5,492,304 | 2/1996 | Smith et al. ............................. 604/256 |
| 5,496,280 | 3/1996 | Vandenbroek et al. .................. 604/167 |

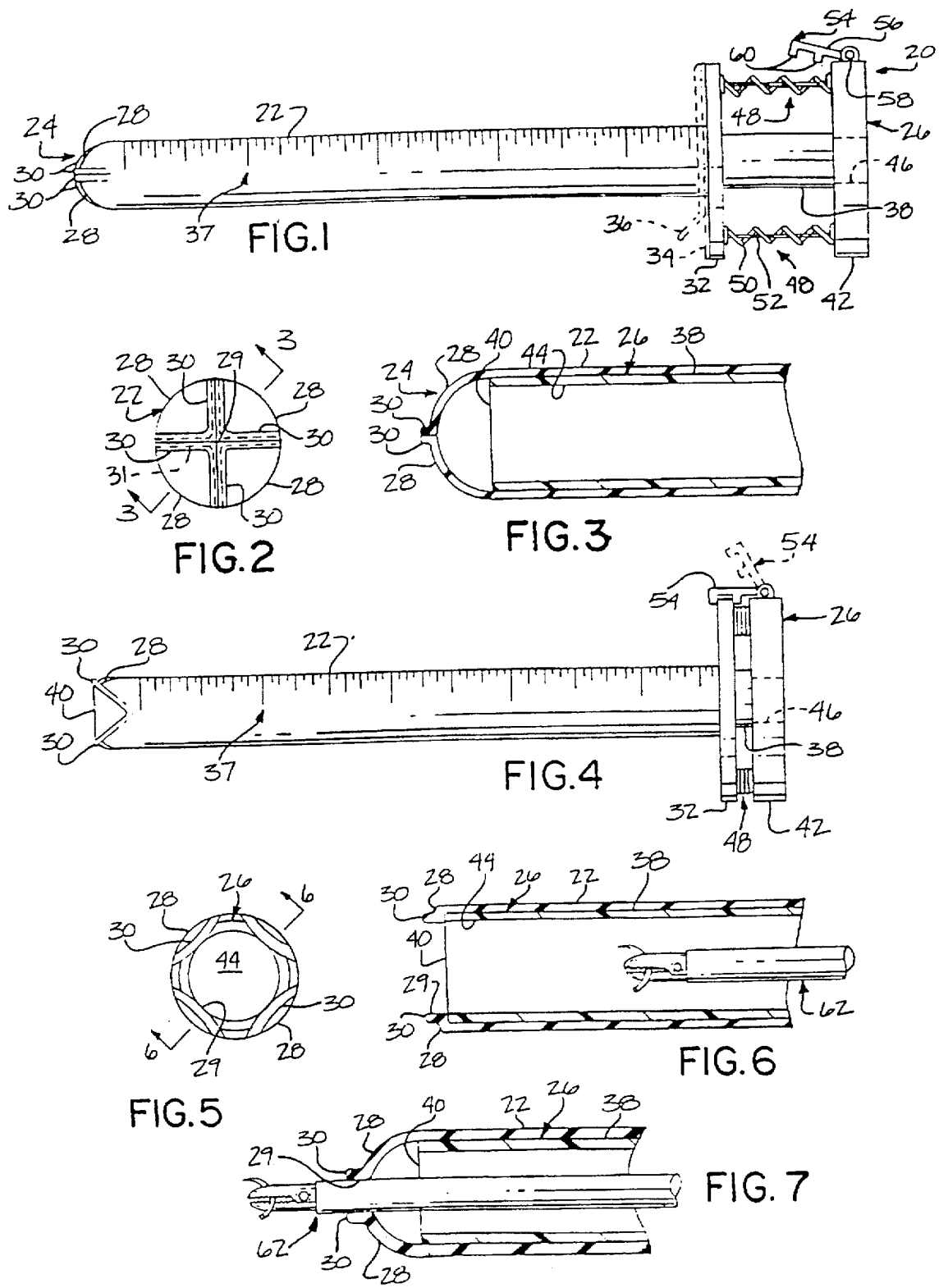

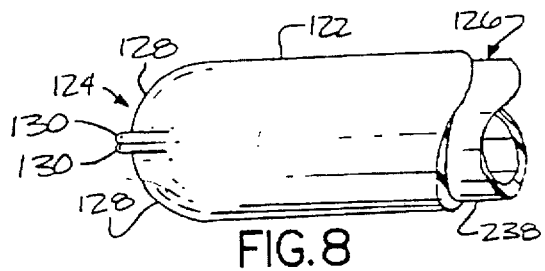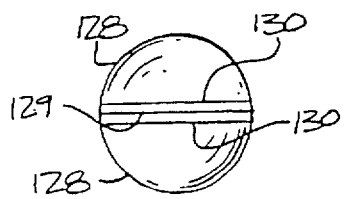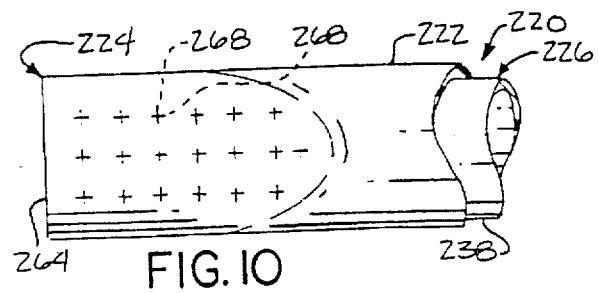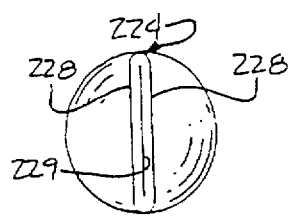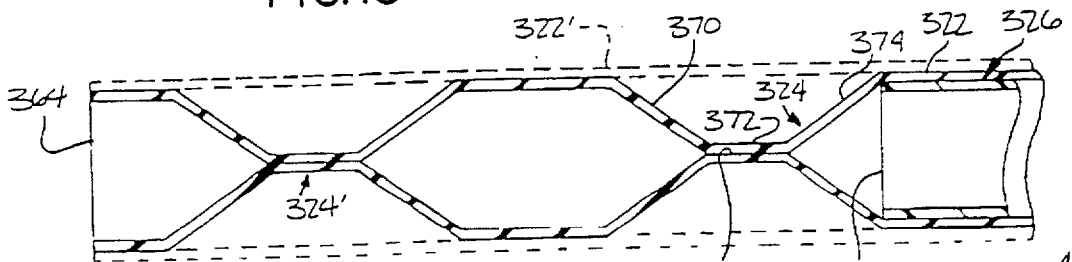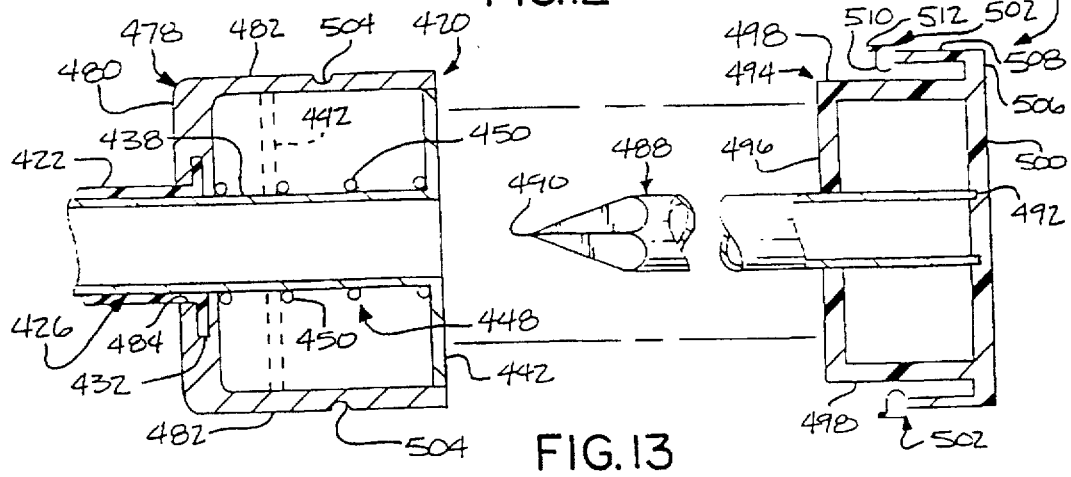

5,797,888

1

CANNULA WITH UNIVERSAL SEAL AND METHOD OF INTRODUCING INSTRUMENTS THERETHROUGH

REFERENCE TO RELATED APPLICATIONS

This application is a continuation-in-part of copending patent application Ser. No. 08/618,328, filed Mar. 19, 1996, the disclosure of which is incorporated herein by reference.

BACKGROUND OF THE INVENTION

1. Field of the Invention

The present invention pertains to medical instruments and, more particularly, to a cannula with a valve or seal for preventing fluid flow through the cannula and to methods of introducing instruments through such a cannula.

2. Discussion of the Related Art

In endoscopic procedures, a cannula in the form of a portal sleeve is normally disposed in the wall of an anatomical cavity such that a distal end of the portal sleeve is positioned within the cavity and a proximal end of the portal sleeve is disposed externally of the cavity to provide a passage establishing communication with an internal site in the cavity from externally of the cavity. Typically, various medical instruments are introduced at the internal site through the portal defined by the portal sleeve in order to perform diagnostic and/or surgical procedures, with the instruments many times having varying sizes in cross-section. In endoscopic procedures, it is important to prevent undesired fluid flow to and from the internal site; and, accordingly, it is desirable for the portal to be sealed prior to and subsequent to the introduction of instruments and while the instruments are in place. In particular, fluids such as gaseous phase carbon dioxide or nitrous oxide are normally introduced in the body for insufflation as part of the endoscopic procedure, and the escape of such gases should be prevented.

Typically, medical instruments are inserted into the portal sleeve via a valve housing mounted externally of the anatomically cavity wall at the proximal end of the portal sleeve. The valve housing is provided with a valve, such as a flapper valve, that opens when a medical instrument is inserted into the portal sleeve and closes when the medical instrument is removed from the portal sleeve. A disadvantage of prior art portal sleeves with valve housings is that the valve housings can protrude from the patient's body, complicating the operating theater space and increasing the length of medical instruments inserted through the portal sleeve during medical procedures.

Another disadvantage of prior art portal sleeves is that they typically include valves having a valve passage of fixed size. Instruments larger in size than the fixed size of the valve passage cannot be inserted through the valve passage into the portal sleeve; and, when instruments smaller in size than the fixed size of the valve passage are inserted, fluid can escape past the smaller size instruments. Universal seals having variable size passages for receiving and sealingly engaging instruments of various sizes are known. Many of these universal seals are made of elastic tearable materials, and instruments inserted through the variable size passages come in contact with the tearable materials. Accordingly, there is a risk that the seals may be torn or punctured when instruments are inserted or withdrawn, particularly where the instruments inserted are sharp. In order to avoid tearing by the inserted instruments, more rigid protectors have been disposed within the seal; however, such seals, even with

2 protectors, still have the disadvantages of being opened by contact with an instrument to be introduced and, thus, creating an obstruction to introduction of the instrument and the opportunity for tearing of the seal causing undesirable leakage of gas. Additionally, prior art universal seals increase resistance to introduction and withdrawal of instruments due to contact of the instruments with the seal and can adversely affect the instrument being inserted by such contact.

SUMMARY OF THE INVENTION

Accordingly, it is a primary object of the present invention to overcome the aforementioned disadvantages of the prior art and to improve cannulas of the type used to create a passage through the wall of an anatomical cavity by incorporating a seal along the tubular body of the cannula and providing a tubular pusher or expander movable within the tubular body to open the seal.

Another object of the present invention is to minimize portions of a cannula disposed externally of an anatomical cavity wall while preventing undesired fluid flow through the cannula prior to and subsequent to the introduction of instruments and while the instruments are in place.

A further object of the present invention is to bias a seal to a normally closed position along the tubular body of a cannula while permitting introduction and withdrawal of instruments through the cannula without the instruments contacting the seal.

Yet another object of the present invention is to automatically open a seal along the tubular body of a cannula as medical instruments are inserted through the cannula and to automatically close the seal when the medical instruments are withdrawn.

Some of the advantages of the present invention over the prior art are that the seal disposed along the tubular body of the cannula can be utilized in place of conventional trocar or portal valves or in combination with conventional trocar or portal valves, that instruments inserted through the seal do not present a significant risk of damage to the seal since no contact is made by the introduced instruments with the seal during insertion, that the seal can be opened to permit introduction or withdrawal of an instrument without contact adverse to either the instrument or devices or tissue carried by the instrument, that opening of the seal is easily accomplished, that the need for separate protectors is eliminated, that the cannula can be configured with or without an external valve housing, that a seal at the distal end of the cannula can be configured to form a blunt or rounded tip for increased safety or a sharp tip for penetrating anatomical tissue, that the cannula can be used with standard trocars, safety shielded trocars and retractable and/or protruding safety penetrating instruments to more fully protect the penetrating tips of the instruments, and that the cannula can be inexpensively manufactured to be economically disposable for single patient use or sterilizable for reuse.

These and other objects, advantages and benefits are realized with the present invention as characterized in a cannula including an elongate tubular body having a distal end adapted to be disposed within the anatomical cavity and a proximal end adapted to be disposed externally of the anatomical cavity, a seal disposed along the tubular body and having a variable size passage to permit instruments of varying sizes to be passed therethrough, and a tubular pusher disposed in the tubular body and insertable in the seal to move the seal from a closed position where the variable size passage is closed to an open position where the variable size passage is open to allow instruments of various sizes to be introduced through the tubular body without contacting the seal. The tubular pusher is withdrawable from the seal such that the seal is biased toward the closed position to contact instruments of various sizes in the passage to form a seal therewith. The tubular pusher is also preferably biased proximally relative to the tubular body to a retracted position where a distal end of the pusher is proximally spaced from the seal. A locking mechanism can be used to lock the tubular pusher in an extended position where the distal end of the tubular pusher is inserted into the seal.

Another aspect of the present invention is generally characterized in a method of introducing an instrument in an anatomical cavity using a cannula having an elongate tubular body with proximal and distal ends, a seal disposed along the tubular body and including a seal member biased to a closed position preventing fluid flow through the tubular body, and a pusher disposed in the tubular body and insertable in the seal to move the seal member from the closed position to an open position, the method including the steps of introducing the distal end of the tubular body in the anatomical cavity, moving the pusher into the seal to cause the seal member to move from the closed position to the open position, introducing the instrument through the pusher such that the instrument extends through the seal, and advancing the instrument distally through the tubular body of the cannula and the pusher into the anatomical cavity. The pusher is withdrawn from the seal with the instrument in place so that the seal member resiliently engages the instrument and forms a seal therewith, after which the pusher can, if desired, be moved into the seal again to open the seal allowing the instrument to be withdrawn without contacting the seal.

Other objects and advantages of the present invention will become apparent from the following description of the preferred embodiments taken in conjunction with the accompanying drawings wherein like parts in each of the several figures are identified by the same reference numerals or by reference numerals having the same last two digits.

BRIEF DESCRIPTION OF THE DRAWINGS

FIG. 1 is a side view, in elevation, of a cannula according to the present invention.

FIG. 2 is a front view, in elevation, of the cannula of FIG. 1 showing a universal seal at the distal end of the cannula in a closed position.

FIG. 3 is a fragmentary sectional side view, taken through line 3—3 in FIG. 2, showing a tubular pusher in a retracted position within the cannula.

FIG. 4 is a side view, in elevation, of the cannula of FIG. 1 showing the universal seal in an open position.

FIG. 5 is a front view, in elevation, of the cannula of FIG. 1 with the universal seal in the open position.

FIG. 6 is a fragmentary sectional side view, taken through line 6—6 in FIG. 5, showing the tubular pusher in an extended position opening the universal seal and a medical instrument being inserted through the cannula.

FIG. 7 is a fragmentary side view, partly in section, of the cannula of FIG. 1 showing the universal seal at the distal end of the cannula sealingly engaging a medical instrument inserted therethrough.

FIG. 8 is a fragmentary side view, in elevation, of a modification of the cannula according to the present invention.

FIG. 9 is a front view, in elevation, of the modified cannula shown in FIG. 8.

FIG. 10 is a fragmentary side view, in elevation, of another modification of the cannula according to the present invention.

FIG. 11 is a front view, in elevation, of the modified cannula shown in FIG. 10.

FIG. 12 is a fragmentary side view, in elevation and partial section, of yet another modification of the cannula according to the present invention.

FIG. 13 is an exploded side view, partly in section, of a modification of the cannula according to the present invention in combination with a medical instrument in the form of a penetrating unit.

DESCRIPTION OF THE PREFERRED EMBODIMENTS

The cannula of the present invention can be utilized to provide access to any type of anatomical cavity; and, accordingly, while the cannula is described hereinafter for use as a portal sleeve in endoscopic procedures, such as laparoscopy, it will be appreciated that the cannula can also be used as a catheter, needle, safety shield or other tubular component of a medical instrument to provide access to small cavities, such as veins and arteries, as well as large cavities, such as the abdomen.

A cannula 20 according to the present invention, as illustrated in FIGS. 1–3, includes an elongate tubular body or sleeve 22 with a universal seal or valve 24 at a distal end and a tubular pusher or expander 26 slidably disposed within the tubular body. Tubular body 22 can have any desirable configuration in cross-section including, but not limited to, circular cylindrical, elliptical or polygonal cross-sectional configurations, in accordance with the procedure to be performed and the anatomical cavity to be penetrated. The tubular body can be made of any suitable, medically acceptable material including rigid materials such as stainless steel, but is preferably made of an expandable, stretchable or elastic medical grade material such as, for example, TECOFLEX manufactured by Thermedics, Inc., TEFLON, GORTEX or elastomeric materials such as silicone or latex rubber.

Universal seal 24 is formed at the distal end of the tubular body and includes four seal members or flaps 28 defining a passage 29 of variable size. The seal members or flaps are normally biased to a closed position when no instrument is passed through the cannula and each have a generally spherical triangular shape with peripheral edges or sides that contact one another when closed to form a generally hemispherical or rounded tip at the distal end of the tubular body. Lips 30 extend outwardly or protrude from the sides of each flap to form a cross-like formation or ridge on the rounded tip when the seal is closed. The lips increase the surface area along respective sides of the flaps to improve contact with instruments passed through the seal and to prevent jamming of tissue when the seal closes. The seal can be made of any suitable, medically acceptable material, but is preferably made of one of the expandable, stretchable or elastic medical grade materials listed above so that it can substantially conform to the shape of medical instruments passed through the tubular body and return to a closed position sealing the distal end of the tubular body when the instruments are removed. The seal members can be maintained in or biased to a closed, initial contracted position by a spine, shown by broken lines in FIG. 2 at 31, including a plurality of individual spring wires or stiffeners attached to the seal members. The spring wires can be disposed on the surface of the seal members or within the material forming the seal members. In the case of the seal members shown, the spring wires are disposed within the material of the seal and oriented along the lips to establish and/or maintain the configuration of the seal member in the closed position. The spring wires or stiffeners can be made of any suitable resilient material but are preferably formed of a material such as a spring steel having a stiffness equal to or greater than that of the flaps. If the tubular body is made of the same material as the seal, the seal and tubular body can be formed as an integral one-piece unit as shown. Alternatively, the seal and tubular body of the cannula can be made of different materials and joined together using conventional techniques, such as bonding, to form an integral unit.

Tubular body 22 terminates proximally at an outwardly extending flange 32 which forms a circular ring around the open proximal end of the tubular body and is suitably dimensioned to prevent the tubular body from being pushed through the wall of the anatomical cavity. The flange can also provide a surface for attaching the cannula to the anatomical cavity wall. For example, in FIG. 1, a thin layer of medical adhesive is carried on the distal face of flange 32, as shown by broken lines at 34, for engaging an anatomical cavity wall to bond with the cannula. The adhesive 34 is backed by a covering, shown by broken lines at 36, which can be peeled away from the adhesive or otherwise removed to expose the adhesive prior to use. A scale 37 including a plurality of indicia lines is provided along an outer or external surface of tubular body 22. The indicia lines are located at predetermined or defined distances from the distal end of the tubular body and from one another allowing the scale to be utilized to take measurements in the body. Various numerical indicia can be provided on the outer surface of the tubular body to identify the distances indicated by the indicia lines.

Pusher 26 includes a hollow, cylindrical body 38 with a distal end 40 disposed in the tubular cannula body and a proximal end mounting an outwardly protruding transverse flange 42. The pusher defines a lumen 44 aligned with the variable size passage defined by valve 24 and an opening 46 in flange 42. A pair of bias members 48 are connected between flanges 32 and 42 to bias the tubular pusher proximally relative to the tubular body to the retracted position, shown in FIGS. 1 and 3, where distal end 40 of the pusher is proximally spaced from valve 24. The bias members are shown as coil springs 50 disposed concentrically around telescoping rods 52 extending transversely between the flanges. A locking mechanism 54 includes a latch arm 56 pivotally mounted on a pin 58 secured to flange 42. The latch arm extends distally from flange 42 to terminate at a pair of inwardly extending protrusions 60 spaced to receive therebetween a peripheral or outer edge of flange 32 when the tubular pusher is in the extended position and arm 56 is pivoted or rotated toward the pusher flange as shown in FIG. 4. While bias members 48 are shown as coil springs disposed concentrically around telescoping rods, it will be appreciated that a bias member can be disposed around the tubular body of the pusher and that the bias members can include various types of springs or other bias devices including, but not limited to, compression springs, tension springs, pan springs, leaf springs, rubber or magnets.

In the closed position, shown in FIG. 3, flaps 28 are biased inwardly toward one another, i.e., in the direction of the longitudinal axis of tubular body 22, such that lips 30 contact one another with little or no gaps or spaces between the lips so that the variable size passage defined by seal 24 is completely closed when the seal is in the closed position prior to receiving an instrument. Since the variable size passage of the seal is completely closed in the closed position, the seal can be utilized in place of conventional trocar or portal valves to prevent fluid flow through the cannula when no instruments are inserted through the cannula. It will be appreciated, however, that the variable size passage of the seal does not have to be completely closed in the closed or initial position and that the seal can be utilized with conventional trocar or portal valves, such as flapper and trumpet valves, disposed along the tubular body of the cannula according to the present invention or disposed within a valve housing attachable to the proximal end of the cannula.

Universal seal 24 is movable to an open, expanded or stretched position wherein the flaps are moved outwardly away from one another, i.e., in a direction away from the tubular body longitudinal axis, to be spread apart from one another such that the variable size passage is open. The flaps are spreadable apart a variable extent or distance such that the passage can be of variable cross-sectional shape and size.

To use cannula 20, the distal end of tubular body 22 is disposed at an internal site in the body, and the proximal end of the tubular body is disposed externally of the body such that the tubular body provides a passage or portal establishing communication with the internal site from externally of the body. Tubular body 22 is typically positioned to extend through an anatomical wall with the use of a penetrating member, such as a trocar or needle, passing through the lumen of the tubular body via tubular pusher 26 and seal 24. Introduction of the penetrating member through the seal is accomplished in the same manner as described hereinafter for introduction of various size instruments through the cannula. The penetrating member is utilized to penetrate the anatomical wall allowing tubular body 22 to follow the penetrating member through the wall. Once the tubular body has been positioned to extend through the anatomical wall, the penetrating member is withdrawn from the cannula leaving the tubular body in place. After withdrawing the penetrating member from cannula 20, seal 24 is permitted to return to the closed position shown in FIGS. 1–3. With seal 24 disposed in the closed position, lips 30 along peripheral edges of the seal members or flaps 28 are in contact with one another such that the variable size passage defined by the flaps is completely closed. Pusher 26 will be in a rested state or condition with bias member 48 biasing the expander proximally relative to the tubular body to the retracted position. As mentioned above, in the retracted position, distal end 40 of expander 26 will be withdrawn from or disposed proximally of seal members 28 such that the variable size passage along the lips thereof remains closed.

When it is desired to introduce an instrument at the internal site through cannula 20, flange 42 is moved longitudinally, distally relative to tubular body 22 against the bias of springs 50, for example by positioning a thumb or other covering over opening 46 in flange 42 to minimize gas leakage from the internal site and pushing on the flange to move the flange towards the proximal end of the tubular body. Springs 50 will then be in a compressed state or condition as shown in FIG. 4, and pusher 26 will be moved longitudinally, distally into the variable size passage defined by seal members 28. Pusher 26 overcomes the closing force or bias of the seal members and spreads the seal members apart from one another. The seal members are moved outwardly by the pusher in a direction transverse or radial to a longitudinal axis of the cannula causing the seal to be moved from the closed position wherein the variable size passage has a first cross-sectional size to an open position wherein the variable size passage has a second cross-sectional size larger than the first cross-sectional size. Once the distal end of pusher 26 is disposed adjacent the side edges or lips 30 of the seal members 28, the seal will be in a fully open position as shown in FIGS. 4–6 with side edges of the seal members being angularly spaced from one another and the seal members being biased toward the closed position such that inner surfaces of the seal members contact the outer surface of the pusher along the distal end thereof to form a seal therewith preventing fluid flow. Tubular pusher 26 can be locked in the extended position by rotating or pivoting latch arm 56 from the unlocked position shown by broken lines in FIG. 4 to the locked position shown by solid lines so that protrusions 60 at the distal end of the arm are disposed on opposite sides of flange 32. The lumen 44 of pusher 26 provides a passage through the seal such that instruments having various cross-sectional sizes larger than the first cross-sectional size of the passage can be inserted without coming into contact with the seal and without resistance to insertion which would otherwise be presented by the seal members. With the seal maintained in the open position, an instrument 62 having a cross-sectional size the same as or smaller than the cross-sectional size of the pusher lumen can be inserted through the pusher as shown in FIG. 6 for introduction at the internal site. When the distal end of the instrument 62 is disposed distally of seal 24, flange 42 is released or unlocked by rotating latch arm 56 away from flange 32, thereby allowing springs 50 to automatically move the pusher proximally relative to the tubular cannula body to the rest state where the distal end of the pusher is disposed proximally of the seal. Referring to FIG. 7, once the pusher has returned to the retracted position, the seal will no longer be held in an open position and will be free to move to a sealing position with seal members 28 urged toward the closed position to engage the instrument 62 to form a seal therewith while allowing the instrument to be moved longitudinally through the variable size passage.

Instrument 62 is withdrawn from cannula 20 by moving flange 42 distally relative to tubular body 22 to cause pusher 26 to enter variable size passage 29 so as to be disposed between the instrument and seal members 28. The instrument is then withdrawn through the pusher, after which flange 42 is released to allow seal 24 to automatically return to the closed or initial position.

FIGS. 8 and 9 illustrate a modification of the cannula according to the present invention wherein the modified cannula 120 includes a tubular body 122 similar to tubular body 22 with a seal 124 at a distal end like seal 24 but with two resilient seal members or flaps 128. Seal members 128 cooperate to define a rounded distal end of generally hemispherical configuration when closed and include outwardly extending edges or lips 130 that are normally biased together in opposed relation to form a seal at the distal end of the cannula. The seal is opened by advancing a tubular pusher 126 distally relative to the tubular body in the manner described above.

FIGS. 10 and 11 illustrate another modification of the cannula according to the present invention wherein the modified cannula 220 includes a tubular body 222 similar to those described above but with a flattened distal end 264 having laterally opposed sides 228 biased together in sealing relation like seal members to form a valve or seal 224. A plurality of spaced spring members, shown by broken lines at 268, are similar to spring members 31 described above and are embedded or otherwise mounted at the distal end of the tubular body and are appropriately oriented, for example in lateral and longitudinal directions as shown, to bias the laterally opposed sides of the distal end of the tubular body to a flattened condition. The laterally opposed sides 228 of the seal 224 normally contact one another across the width of the tubular body to form a seal closing the distal end of the tubular body when no instruments are passed through the cannula. The seal can be opened in the manner described above by moving the tubular pusher 226 distally relative to the tubular body and, when the tubular expander is retracted, the opposed sides or seal members of the seal will move resiliently toward the flattened condition against any instrument passed through the tubular body to prevent fluid flow around the instrument.

The modified cannula 320 shown in FIG. 12 includes a tubular body 322 formed of an expandable, stretchable and resilient material and having a valve or seal 324 disposed proximally of the tubular body distal end 364. Seal 324 includes a generally frusto-conical forward section 370 of decreasing cross-sectional size in a proximal direction and a generally cylindrical or tubular intermediate section 372 connecting the forward seal section with a generally frusto-conical rearward seal section 374 of increasing cross-sectional size in a proximal direction. Intermediate seal section 372 defines a variable size passage 329 axially aligned with a longitudinal axis of the tubular body. In the retracted position shown, distal end 340 of the tubular pusher 326 is disposed proximally of the intermediate section so that inner surfaces of the intermediate seal section of the seal contact one another to cause the variable size passage of the seal to be completely closed prior to receiving an instrument. The seal can be opened all or part-way by advancing the tubular pusher distally relative to the tubular body in the manner described above.

The cannula according to the present invention can be provided with any number of valves or seals along its length. For example, in FIG. 12, a second seal, shown by solid lines at 324', can be mounted at the distal end of tubular body 322 and opened with a tubular pusher. Furthermore, any of the seals disclosed herein can be disposed within a relatively rigid tubular body or outer sleeve, as indicated by broken lines at 322' in FIG. 12, to form a valve or seal within a tubular body or sleeve.

Another modification of the cannula according to the present invention is illustrated in FIG. 13 at 420 in combination with an instrument in the form of a penetrating unit 476. The modified cannula 420 is similar to the cannulas described above and, in addition, includes a housing 478 mounting a proximal end of tubular body 422. Housing 478 includes a front wall 480 disposed perpendicular to a longitudinal axis of the tubular body and side walls 482 extending transversely from the front wall to an open proximal end of the housing. Tubular body 422 extends through an opening 484 in the front wall of the housing and terminates at flange 432 which is disposed within a recess formed in the front wall. Tubular expander or pusher 426 is similar to the tubular pushers described above and includes a tubular member 438 telescopically received within the tubular cannula body and terminating proximally at a flange 442 configured to slide longitudinally within the housing. Bias member 448 is shown as a coil spring 450 disposed concentrically around the tubular pusher and held in compression between front wall 480 of the housing and flange 442 of the expander.

Penetrating unit 476 includes a penetrating member 488 having a sharp distal tip 490 and a proximal end 492 mounted by a housing 494. Housing 494 includes a front wall 496 disposed perpendicular to a longitudinal axis of the penetrating member and side walls 498 extending transversely between the front wall and a rear wall 500. A pair of locking detents 502 extend from a proximal end of the housing to couple with recesses 504 formed in side walls 482 of the housing, respectively, when the penetrating unit is fully inserted into the cannula. Locking detents 502 each include an arm 506 extending laterally outward from housing rear wall 500 to a distally extending arm 508 which terminates in an inwardly extending detent or protrusion 510 with a finger release 512.

In use, bias member 448 normally biases tubular pusher 426 in a proximal direction to a retracted position where flange 442 is disposed adjacent the proximal end of portal housing 478. In the retracted position, the distal end of the tubular pusher will be proximally spaced from a valve or seal along the tubular body of the cannula. When it is desired to penetrate an anatomical cavity wall, penetrating unit 476 is advanced distally relative to the cannula to cause the penetrating member 488 to slide within the tubular pusher until front wall 496 of the penetrating unit abuts flange 442 of the tubular pusher. Further distal movement of the penetrating unit causes the flange 442 of the pusher to move distally against the bias of spring 450 while at the same time causing the distal end of the tubular pusher to be extended through the seal of the cannula to provide a passage through the seal for the sharp tip of the penetrating member. When the tubular pusher is fully extended as shown by broken lines in FIG. 13, detents 510 of the locking mechanism will engage recesses 504 in the portal housing to lock the penetrating member in place relative to the portal housing such that the sharp, distal tip 490 of the penetrating member protrudes from the distal end of tubular body 422 to penetrate the anatomical cavity wall. The penetrating member may then be used to penetrate through anatomical tissue to gain access to an anatomical cavity in the body, after which the penetrating unit may be removed from the cannula by lifting release levers 512 away from the portal housing in a lateral direction to cause detents 510 to move out of recesses 504 and by then withdrawing the penetrating unit in a proximal direction relative to the cannula until the tip is removed from the expander. As the penetrating unit is withdrawn proximally, bias member 448 will move the tubular expander proximally relative to the portal housing causing the distal end of the tubular expander to become proximally spaced from the seal which will automatically close to seal the cannula so that fluids cannot pass therethrough.

From the above, it will be appreciated that the cannula according to the present invention can be used to establish a portal or passage through any type of anatomical cavity wall allowing medical instruments to be introduced at an internal site within the anatomical cavity while preventing undesired fluid flow to and from the internal site by use of a valve or seal disposed along the cannula. The seal can have any configuration to prevent fluid flow through the cannula prior to the introduction of instruments through the cannula, after the instruments are withdrawn from the cannula and/or while the instruments are in place. For example, the seal can be configured as a conventional trumpet or flapper valve, as a resilient membrane with an aperture formed therethrough, as a universal seal as described in my copending patent application Ser. No. 08/618,328, filed Mar. 19, 1996, pending, and incorporated herein by reference, or as a distal end valve as described in my copending patent application Ser. No. 08/383,520, filed Feb. 3, 1995, the disclosure of which is incorporated herein by reference.

By placing the seal along the tubular body or sleeve of the cannula, portions of the cannula disposed externally of the anatomical cavity wall can be minimized. If the seal member sealingly engages a surface of the tubular body or other seal members in the closed position, the seal can be used in place of a conventional valve housing to prevent undesired fluid flow to and from the internal site when no instruments are inserted through the cannula. If, on the other hand, the seal member or members are configured to define a passage or opening which is not completely closed in the initial position, but which is smaller in cross-sectional size than an instrument to be inserted, the cannula can be used in combination with valves or seals that do close completely in the initial position and/or with known valve housings to prevent fluid flow to and from the internal site when no instruments are inserted through the cannula.

In order to prevent damage to the seal or to instruments inserted through the seal, a tubular expander or pusher with a blunt configuration is used to open the seal so that the instruments can be inserted through the seal via the pusher without contacting the seal. The pusher is preferably made of a rigid material such as, for example, a suitable medical grade plastic or metal material, and can have any configuration to open the seal. For example, the pusher can be provided with slots or configured with a spiral cross-section to permit expansion of the pusher in a radial direction transverse to a longitudinal axis of the sleeve. If the tubular body of the cannula is formed of an expandable, stretchable and resilient material, the pusher will impart a shape to the tubular body while being slidably movable therein to open the seal. The tubular cannula body and pusher can have any configuration in cross-section including, but not limited to, cylindrical, elliptical and polygonal cross-sectional configurations.

The pusher can be biased proximally or distally relative to the tubular cannula body or can be unbiased, if desired. While a locking mechanism in the form of a latch arm is shown for locking the pusher in the extended position, the pusher can be locked in the extended or retracted positions or any position inbetween using any type of locking mechanism including, but not limited to, latch arms, ratchets and frictional couplings. The cannula can also be provided without a locking mechanism, if desired.

When the seal is disposed at the distal end of the tubular cannula body, it can be configured in a manner to form relatively smooth, blunt surfaces or to penetrate anatomical tissue when closed. Also, the seal can be formed with the tubular body as an integral onepiece unit or the seal can be formed as a separate unit and connected with the tubular body in an integral or detachable manner, for example, by threaded engagement, bonding, hinged connection or any other suitable means of attachment. Furthermore, stiffeners such as spring members can be embedded in any of the seals and in any orientation relative to a longitudinal axis of the tubular body to provide reinforcement and to bias the seals to a closed or initial condition.

Depending on the type of tissue and the size of the opening through which the cannula is inserted, the cannula can be held in place or anchored by frictional engagement of the tubular body with the wall of the anatomical cavity, medical adhesives, tape, sutures, stabilizers or by use of any other medically acceptable method of attachment. In the case of sutures, the flange at the proximal end of the sleeve can be formed with one or more circumferentially spaced apertures or eyelets to facilitate passage of the suture material through the flange and into the anatomical tissue. The cannula can also be anchored by use of one or more tissue penetrating members carried by the cannula, for example as disclosed in applicant's copending patent application Ser.

No. 08/243,493, filed May 16, 1994, now U.S. Pat. No. 5,653,718 the disclosure of which is incorporated herein by reference.

The cannula can be provided with a distensible or inflatable membrane, for example as disclosed in applicant's copending patent application Ser. No. 08/383,520, filed Feb. 3, 1995, now abandoned the disclosure of which is incorporated herein by reference. When such a membrane is provided, it can be placed anywhere on the tubular body and can be a flaccid, bag-like membrane that hangs loosely from the tubular body of the cannula when deflated, or the membrane can be a stretchable, elastic membrane that conforms closely to the exterior shape of the sleeve in a deflated or unexpanded condition. Furthermore, any number of membranes can be positioned on the sleeve and communicated with a single, common valve or multiple valves as desired.

The cannula of the present invention is also advantageous when used with needles, standard trocars and penetrating instruments of the type that move penetrating components relative to one another to protect tissue penetrating tips of the instruments upon entering an anatomical cavity. For example, the cannula of the present invention could be used with penetrating instruments having retractable penetrating members, with penetrating instruments of the type that move the cannula and/or a safety member, such as a shield or probe, distally relative to the penetrating member upon penetrating into an anatomical cavity, or penetrating instruments that retract a penetrating member while causing the cannula and/or a safety member such as a shield or probe to protrude. When the cannula of the present invention is used with a penetrating instrument that permits relative movement between the tubular body of the cannula and a penetrating member such that the tip of the penetrating member is proximally spaced from the seal in the tubular body of the cannula, it will be appreciated that the seal can be made to close around the penetrating member, providing enhanced safety and that any housings mounting the cannula can be configured to be detached from the cannula once the cannula is placed in the wall of the anatomical cavity.

The components of the cannula can be made of any suitable, medical grade materials to permit sterilization for reuse or disposal for single patient use and can be made of multiple parts of various configurations and materials to reduce cost. The features of the various embodiments described above can be combined in any manner desired dependent upon the procedural requirements and the complexity of the cannula.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A cannula for insertion through an anatomical cavity wall to establish communication with the anatomical cavity, said cannula comprising an elongate tubular body having a distal portion adapted to extend through the anatomical cavity wall into the anatomical cavity and a proximal portion adapted to be disposed externally of the anatomical cavity;

a seal disposed along said distal portion of said tubular body and having a variable size passage to permit instruments of varying sizes to be passed therethrough, said seal being biased toward a closed position wherein said variable size passage is closed and being movable to an open position wherein said variable size passage is open; and a tubular pusher disposed in said tubular body and insertable in said seal to move said seal from said closed position to said open position allowing instruments of various sizes to be introduced through said tubular body without contacting said seal, said tubular pusher being withdrawable from said seal such that said seal is biased toward said closed position to contact instruments of various sizes in said passage;

said seal having a configuration to sealingly engage instruments of various sizes in said passage when said pusher is withdrawn from said seal.

2. A cannula as recited in claim 1 wherein said seal is disposed at said distal end of said tubular body.

3. A cannula as recited in claim 1 wherein said seal is disposed in said tubular body.

4. A cannula as recited in claim 1 and further comprising a plurality of seals disposed along said tubular body in spaced relation.

5. A cannula as recited in claim 1 wherein said seal includes a plurality of seal members biased together to a closed position wherein said variable size passage is closed.

6. A cannula as recited in claim 5 wherein opposed, peripheral edges of said seal members contact one another in said closed position to prevent fluid flow through said tubular body.

7. A cannula as recited in claim 5 wherein opposed, peripheral edges of said seal members turn outwardly to form lips.

8. A cannula as recited in claim 5 wherein said seal members are formed of a resilient material.

9. A cannula as recited in claim 1 wherein said seal includes a seal member formed of a resilient material.

10. A cannula as recited in claim 9 and further comprising at least one resilient spring member of predetermined shape mounted by said seal to bias said seal member toward said closed position.

11. A cannula as recited in claim 1 and further comprising pusher bias means for biasing said tubular pusher proximally relative to said tubular body to a retracted position where a distal end of said tubular pusher is proximally spaced from said seal.

12. A cannula as recited in claim 11 and further comprising a locking mechanism to lock said tubular pusher in an extended position where said distal end of said tubular pusher is inserted into said seal.

13. A cannula as recited in claim 1 and further comprising a housing mounting proximal ends of said tubular body and said tubular pusher.

14. A cannula for insertion through an anatomical cavity wall to establish communication with the anatomical cavity, said cannula comprising an elongate tubular body having a distal end adapted to be disposed within the anatomical cavity and a proximal end adapted to be disposed externally of the anatomical cavity;

a seal disposed along said tubular body and having a variable size passage to permit instruments of varying sizes to be passed therethrough, said seal being biased toward a closed position wherein said variable size passage is closed and being movable to an open position wherein said variable size passage is open; and a tubular pusher disposed in said tubular body and insertable in said seal to move said seal from said closed position to said open position allowing instruments of various sizes to be introduced through said tubular body without contacting said seal, said tubular pusher being withdrawable from said seal such that said seal is biased toward said closed position to contact instruments of various sizes in said passage to form a seal therewith;

wherein said tubular body is formed of a flexible material having the ability to stretch to accommodate instruments of various size.

15. In combination, a cannula and a medical instrument for insertion through said cannula, said cannula comprising an elongate tubular body having a distal end adapted to be disposed within the anatomical cavity and a proximal end adapted to be disposed externally of the anatomical cavity;

a seal disposed along said tubular body and having a variable size passage to permit instruments of varying sizes to be passed therethrough, said seal being biased toward a closed position wherein said variable size passage is closed and being movable to an open position wherein said variable size passage is open;

a tubular pusher disposed in said tubular body and insertable in said seal to move said seal from said closed position to said open position allowing instruments of various sizes to be introduced through said tubular body without contacting said seal, said tubular pusher being withdrawable from said seal such that said seal is biased toward said closed position to contact instruments of various sizes in said passage to form a seal therewith; and a housing mounting proximal ends of said tubular body and said tubular pusher;

wherein said tubular pusher of said cannula includes a flange movable within said housing and said medical instrument has a configuration to abut said flange during insertion to open said seal.

16. A method of introducing an instrument in an anatomical cavity using a cannula having an elongate tubular body with a proximal portion and a distal portion, a seal disposed along the distal portion of the tubular body and including a seal member biased to a closed position preventing fluid flow through the tubular body, and a tubular pusher disposed in the tubular body and insertable in the seal to move the seal member from the closed position to an open position, said method comprising the steps of introducing the distal portion of the tubular body in the anatomical cavity;

moving the tubular pusher into the seal to cause the seal member to move from the closed position to the open position;

introducing the instrument through the tubular pusher such that the instrument extends through the seal;

advancing the instrument distally through the tubular body of the cannula and the tubular pusher into the anatomical cavity; and withdrawing the tubular pusher from the seal such that the seal member resiliently engages the instrument and forms a seal therewith.

17. A method of introducing an instrument into an anatomical cavity as recited in claim 16 and further comprising, after withdrawing the tubular pusher from the seal, the steps of moving the tubular pusher into the seal to cause the seal member to move to the open position, and removing the instrument from the anatomical cavity in a proximal direction through the tubular body of the cannula and the tubular pusher.

18. A method of introducing an instrument into an anatomical cavity as recited in claim 16 and further comprising the step of locking the tubular pusher in a predetermined position relative to the tubular body of the cannula.

19. A method of introducing an instrument into an anatomical cavity using a cannula having an elongate tubular body with proximal and distal ends, a seal disposed along the tubular body and including a seal member biased to a closed position preventing fluid flow through the tubular body, and a tubular pusher disposed in the tubular body and insertable in the seal to move the seal member from the closed position to an open position, said method comprising the steps of introducing the distal end of the tubular body in the anatomical cavity;

moving the tubular pusher into the seal to cause the seal member to move from the closed position to the open position;

introducing the instrument through the tubular pusher such that the instrument extends through the seal;

advancing the instrument distally through the tubular body of the cannula and the tubular pusher into the anatomical cavity; and withdrawing the tubular pusher from the seal such that the seal member resiliently engages the instrument and forms a seal therewith;

wherein moving the tubular pusher into the seal includes the step of causing the instrument to abut a proximal end of the tubular pusher and advancing the instrument distally relative to the tubular body of the cannula to cause the tubular pusher to contact the seal member.

* * * * *